United States Patent [19]

Romandetto

[11] Patent Number: 5,018,221

[45] Date of Patent: May 28, 1991

[54] JOINT GUARD

[76] Inventor: Joseph G. Romandetto, 1534 Waring Ave., Bronx, N.Y. 10469

[21] Appl. No.: 333,313

[22] Filed: Apr. 5, 1989

[51] Int. Cl.[5] .......................................... A41D 13/08
[52] U.S. Cl. ............................................. 2/16; 2/20; 2/161 A; 128/878; 128/879
[58] Field of Search ............... 128/87 R, 87 A, 877, 128/878, 879; 2/16, 20, 21, 161 A

[56] References Cited

U.S. PATENT DOCUMENTS

| | | | |
|---|---|---|---|
| 3,398,951 | 8/1968 | Disko | 2/20 |
| 3,606,614 | 9/1971 | Dimitroff | 2/20 |
| 4,051,553 | 10/1977 | Howard | 2/161 A |
| 4,071,913 | 2/1978 | Rector | 2/20 |
| 4,099,269 | 7/1988 | Porner | 2/16 |
| 4,295,229 | 10/1981 | Clark et al. | 2/20 |
| 4,400,829 | 8/1983 | Willis | 2/16 |
| 4,657,000 | 4/1987 | Hepburn | 128/87 R |
| 4,677,971 | 7/1987 | Lindemann | 128/87 R |
| 4,688,269 | 8/1987 | Maeshima | 2/16 |
| 4,748,690 | 6/1988 | Webster | 2/20 |

Primary Examiner—Robert A. Hafer
Assistant Examiner—Kerry Owens

[57] ABSTRACT

An apparatus having a portion of shock absorbing material disposed adjacent to front side of a joint. The shock absorbing material can be configured and dimensioned so as to cushion the respective movements of the bones immediately next to the joint towards each other. In a preferred embodiments the shock absorbing material is attached to a glove and a disposed adjacent a middle joint of one or more forefingers. An apparatus comprising a portion of rigid material disposed adjacent a back side of a joint, wherein the rigid material is provided a bending means so as to allow the rigid material to bend in a manner approximating the natural bending of the joint and the bending means is configured and dimensioned so as to prevent bending of the rigid material to an extend which would be an unnatural bending of the joint. The shock absorbing material and the rigid material can be disposed adjacent opposite sides of the same joint.

10 Claims, 9 Drawing Sheets

JOINT GUARD

FIELD OF THE INVENTION

The present invention relates to the field of protective gear and particularly that type of protective gear adapted to be worn by a person or animal, particularly in sports participant, in order to protect a joint from injury. In one embodiment the present invention especially protects the fingers, including the thumb, and the knuckles from impact related injuries.

BACKGROUND OF THE INVENTION

The prior art includes batting gloves, golf gloves, hockey gloves, knee pads, elbow pads and tape. None of these items of prior art are adapted to prevent impact related injuries including jams and sprains, while allowing natural hand and finger movement.

SUMMARY OF THE INVENTION

As used herein the term "front" when used with respect to a joint defines the side of the joint which the bones immediately above and immediately below the joint will bend towards when the joint bends in a natural manner, and the term "back" when used with respect to a joint defines the side of the joint opposite the front or, in other words, the side of the joint which the bones immediately above and immediately below the joint will not bend towards when the joint bends in a natural manner.

As used herein the term "clothing" defines any article which is fitted over or attached to a portion of a living body, including protective gear and sports equipment.

As used herein the term "adjacent" defines a position near a reference point, and not necessarily immediately alongside the reference point.

As used herein, the term "threshold force" defines a force of sufficient magnitude to remove a shock absorbing material from the item to which it is attached, and applied to the shock absorbing material at any angle which tends to remove the shock absorbing material from the item to which it is attached and includes tensile forces and shear forces.

As used herein the term "prevent" is synonymous with "reducing the possibility of", because stresses of unforeseen magnitude may cause injury despite utilization of a device according to the present invention.

The present invention includes an apparatus comprising a portion of shock absorbing material disposed adjacent a front side of a first joint. The portion of shock absorbing material may be configured and dimensioned so as to cushion respective movements of a bone above the first joint and a bone below the first joint toward each other.

The shock absorbing material may be releasably attached to clothing. Further, the shock absorbing material may be releasably attached to clothing by attachment means having a tear-away threshold so as to allow the shock absorbing material to be removed from the clothing by a threshold force.

The threshold force may be of a magnitude sufficiently low to avoid injury to a second joint adjacent to the shock absorbing material, and the attachment means may be elastic material and thread or interlocking plastic hooks and plastic loops.

The clothing that the shock absorbing material may be attached to can be a glove or more particularly the forefinger of a glove, and the first joint adjacent to which the shock absorbing material is disposed can be a joint of a forefinger.

The present invention also includes providing a portion of shock absorbing material adjacent the front side of a joint of each four forefingers, and this can be done with either four separate segments or one continuous segment of shock absorbing material.

The present invention includes providing a shock absorbing material disposed in the area between the palm of the hand and the front of the fingers. The shock absorbing material is firm yet pliable, thus cushioning any contact between the palm of the hand and the fingers, and thereby minimizing impact injuries to the fingers, knuckles and hand and minimizing the occurence of "finger jamming", a recurring injury wherein fingers are axially thrust into one or all of the respective finger knuckles, and finger sprains, an abnormal twisting of one or more of the finger knuckles.

The present invention also includes a shock absorbing material adjacent the front of the fingers. In this manner the shock absorbing material can be adjusted to the proper point on the face of the fingers to minimize injury to particular fingers and/or particular sets of knuckles, in preparation for a known recurring angle of impact. The shock absorbing, firm yet pliable material may be releasably attached to a glove or may be attached thereto in a fixed manner.

If releasably attached, the means for attaching the shock absorbing material may possess a tear-away threshold so as to allow the shock absorbing material to be torn away from the glove when a certain level of force is applied to the shock absorbing material, thus preventing the shock absorbing material from causing jams and sprains which would not occur in the complete absence of the shock absorbing material. If the shock absorbing material is not releasably attached as such there is a slight possibility that, under certain circumstances, the shock absorbing material could get caught on an object or person thereby causing, rather than preventing, an injury to a joint.

The present invention also includes providing a protective material adjacent the back side of a joint, thus minimizing impact injuries thereto. As used herein, the term "protective material" defines a firm yet pliable shock absorbing material, a rigid or semi-rigid plastic or a metal.

The protective material provided adjacent the backside of the thumb may be provided with a means for allowing the material to bend at points immediately adjacent to one or both of the thumb knuckles. Further, according to the present invention, the means for allowing bending may comprise a means for allowing bending only to a limited extent so as to prevent bending of the thumb to an unnatural extent. In this regard, the natural movement of the thumb is not impaired while impact injuries including sprains and jams are minimized.

The present invention includes an apparatus comprising a portion of protective material disposed adjacent a back side of a joint, the protective material being configured and dimensioned so as to prevent direct impact to the back side of the joint. The protective material can be a rigid material, and the rigid material can be provided with a bending means so as to allow the rigid material to bend in a manner approximating the natural bending of the joint and immediately connecting bones.

The bending means can be configured and dimensioned so as to prevent bending of the rigid material to an extent which would correspond to an unnatural amount of bending for the joint.

A shock absorbing material can be disposed on the joint-side of the rigid material. Also, the rigid material can be provided with a length adjustment means.

The rigid material and the shock absorbing material can be releasably attached to clothing by attachment means and the attachment means can include a plurality of plastic hooks and plastic loops.

The clothing which the rigid material is attached to can be a glove. The joint which the rigid material is disposed adjacent to can be a finger joint or more particularly a thumb joint, and the rigid material can extend at least to the tip of the finger.

The present invention further includes the rigid material and the bending means each being configured and dimensioned so as to prevent the rigid material from bending in a direction opposite the natural bending direction of the joint.

The present invention further includes provided a portion of shock absorbing material adjacent the front side of a joint, and a portion of protective material, such as rigid plastic, adjacent the back side of the joint.

DETAILED DESCRIPTION OF THE PREFERRED EMBODIMENT

In the description which follows, any reference to either orientation or direction is intended primarily for the purpose of illustration and is not intended in any way as a limitation of the scope of the present invention.

While it is presently contemplated that the preferred embodiments of the present invention are devices used for the protection of finger joints, the scope of the present invention includes joints of all types, including vetinary uses.

Figures 1, 1A:
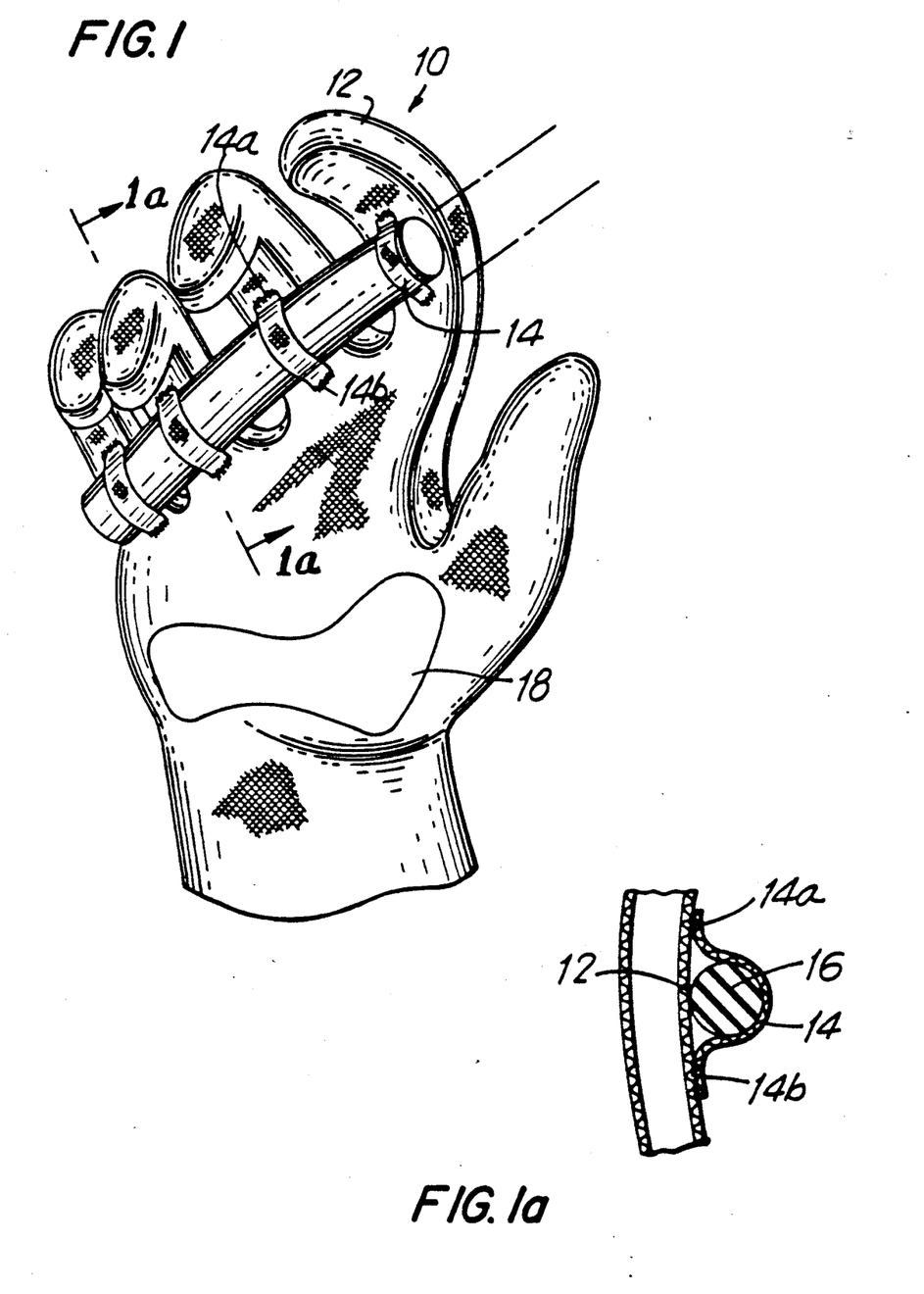
FIG. 1 is a front view of a hand guard according to the present invention.
FIG. 1a is a cross-section view taken along line A—A of FIG. 1.

As shown in FIG. 1 an embodiment of a hand guard 10 according to the present invention may be made by taking a standard close fitting glove 12, such as a golf glove or a batting glove, and attaching to each of the four forefingers a segment of heavy duty elastic 14. The segment of elastic 14 are attached to each forefinger, respectively, at their upper and lower ends 14a, 14b while the sides remain unattached so as to allow for a portion of shock absorbing material 16 such as gortex or putty to be firmly held between the finger portion of the glove and the segment of elastic. Elastic segments 14 are adjacent to the horizontal centerline of the second finger joints, respectively, also known as the PIP joints.

Segment of elastic 14 may have a smooth, slick outer surface so as to minimize friction where desired, such as for a base runner, and may be provided with a thin coating of plastic-like material in this regard. In some applications, such as for a football player, a high friction surface on the palm of the hands is desirable, and elastic segment 14 can have a rough outer surface with a high coefficient of friction in this regard. Elastic segment may be attached to the glove forefingers at upper and lower ends 14a, 14b in a permanent manner by tightly sewing the elastic segments with strong nylon thread. In another embodiment the attachment at upper and lower ends 14a, 14b may be sewn with a less strong thread so as to allow the elastic segments 14 and shock absorbing material 16 to be torn away from the glove 12 when a tear away threshold force is applied to the upper and lower ends 14a, 14b.

A heavy duty wear surface 18 may be provided on the lower part of the palm of glove 12 so as to increase the durability of the hand guard.

Figure 2:
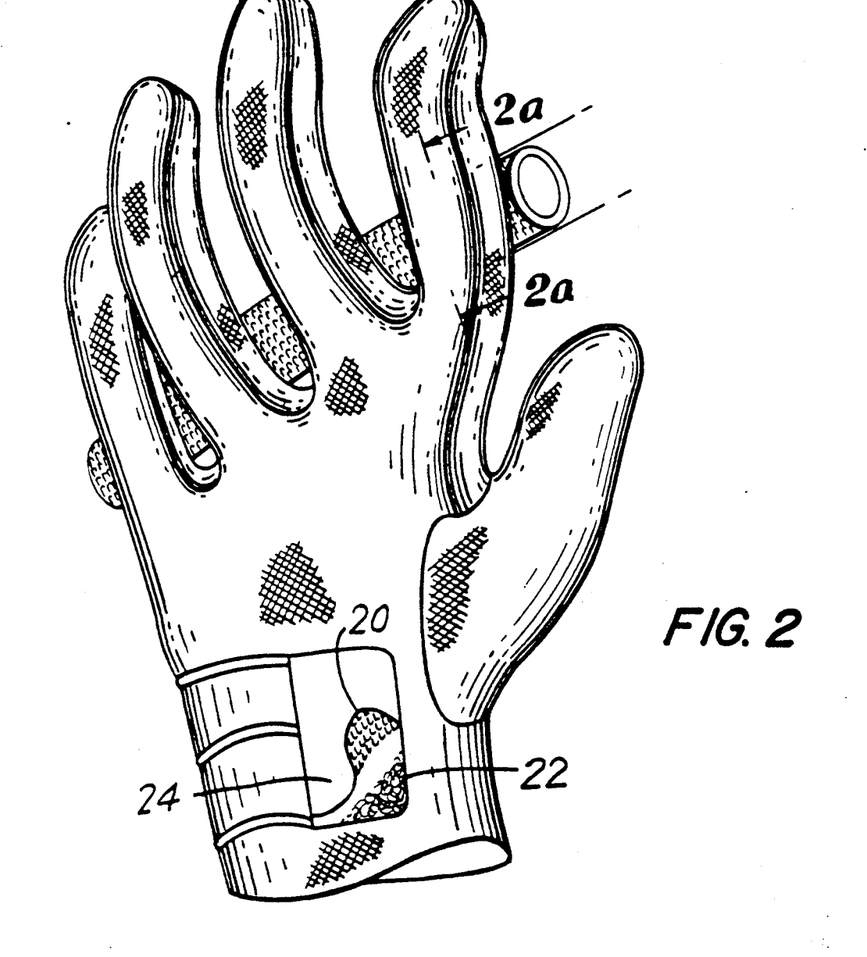
FIG. 2 is a rear view of a hand guard according to the present invention.
Figure 2A:
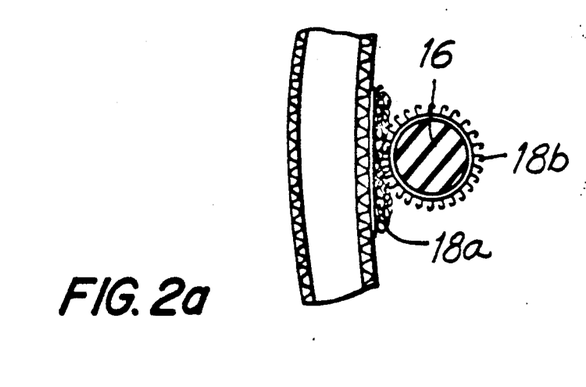
FIG. 2a is a cross-sectional view taken along line B—B of FIG. 2.

FIG. 2 illustrates a rear view of another embodiment of a han guard according to the present invention. The shock absorbing material 16 is a continuous segment extending from the right side of the first forefinger to the left side of the fourth forefinger in between the middle and lower joints of each respective forefinger. In this embodiment each forefinger of glove 12 is provided with a segment of velcro material 18a. Velcro material is commercially available and comprises a two part material wherein the first part is provided with a plurality of plastic hooks and the second part is provided with a plurality of plastic loops, and the two parts are releasably attachable to one another by applying a force pushing them together and may be pulled apart by a threshold force.

The forefingers of glove 12 may be provided with velcro, or equivalent, material 18a provided with a plurality of plastic loops, which is firmly attached thereto by continuous peripheral sewing or adhesive. The segment of shock absorbing material 16 is provided with an outer covering of velcro, or equivalent, material 18b provided with a plurality of plastic hooks, and firmly attached thereto by adhesive. For economical reasons, the velcro covering 18b on the shock absorbing material 16 can be provided only along portions thereof corresponding to the velcro material 18a covering portions of the fingers of the glove 12.

A wrist size adjustment may be provided in order to accomodate varying size hands, and can include velcro material, covering a flap portion 20 and a corresponding portion 22 of the glove palm, and a slit in the glove below the outer end 24 of the flap portion 22.

Figure 12:
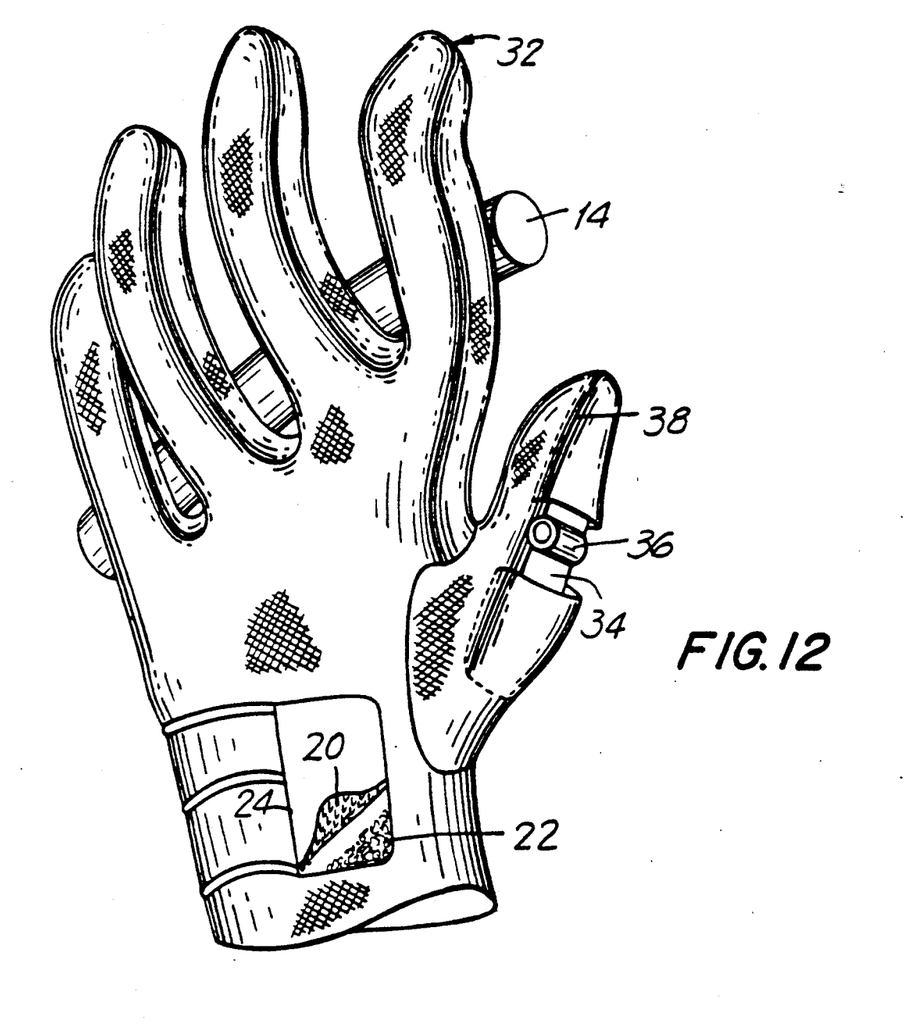
FIG. 12 is a rear view of a hand guard according to the present invention.
Figure 12A:
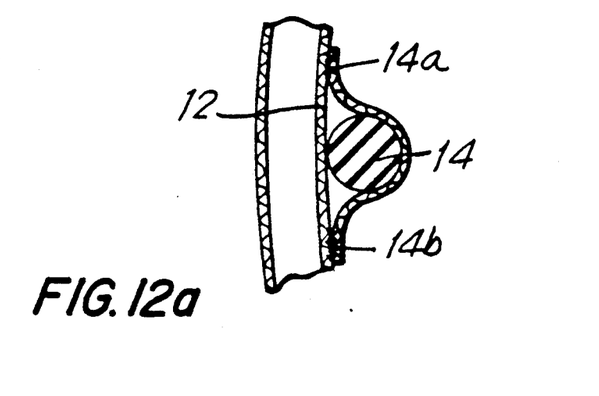
FIG. 12a is a cross-sectional view taken along line B—B of FIG. 12.

FIG. 12 illustrates a rear view of another embodiment of a finger guard according to the present invention wherein a continuous segment of shock absorbing material 14 is provided adjacent the middle joint of each forefinger. In this embodiment, continuous segment of shock absorbing material 14 is attached to glove 32 by segments of elastic material sewn to each forefinger. The sewing thread can be very strong, so as to provide a permanent attachment, or relatively weak so as to allow the shock absorbing material to be removed from the glove by a threshold force so that the presence of the shock absorbing material does not cause any injury. Elastic material and shock absorbing material can be provided with either a smooth or a rough surface texture, depending upon the particular application.

Figure 3:
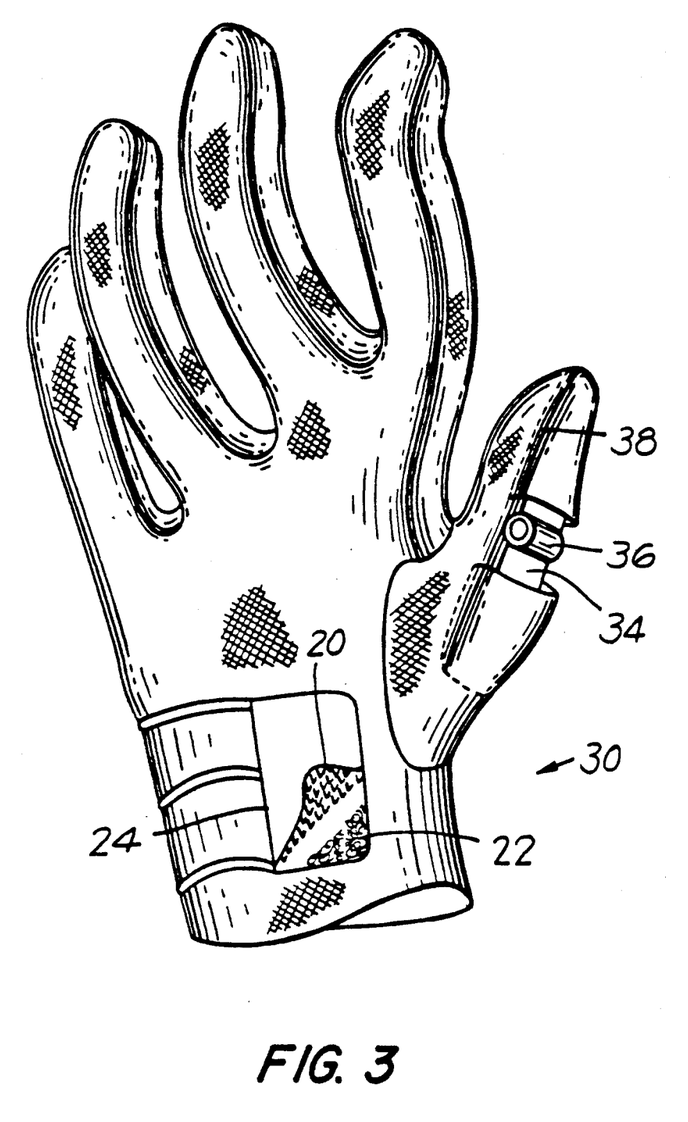
FIG. 3 is a rear view of a hand guard according to the present invention.

FIG. 3 illustrates a thumb guard 30 according to the present invention attached to a batters glove 32 adjacent to the back side of the second or lower thumb joint. The thumb guard includes a portion of rigid material 34 configured and dimensioned to substantially conform to the contour of the thumb and hand. A hinge 36 is provided adjacent the centerline of the second thumb joint so that the rigid material bends when the second thumb joint bends.

The rigid material 34 is held firmly attached to glove 32 by elastic material 37 sewn to the glove. The elastic material 38 can completely cover rigid material 34 or, as shown in FIG. 3, a portion of rigid material 34 adjacent hinge 36 is left uncovered so as not to interfere with bending. In such an embodiment, rigid material 34 can be inserted inbetween glove 32 and elastic material 38 after elastic material 38, in two parts, is sewn to glove 32, leaving the sides adjacent the second thumb joint partially or completely unsewn.

FIG. 3 also illustrates a wrist size adjustment means having a flap portion 20 covered with velcro, a corresponding portion of the glove palm 22 covered with velcro and a slit in the glove palm adjacent the outer end of flap portion 24.

Figures 4, 6:
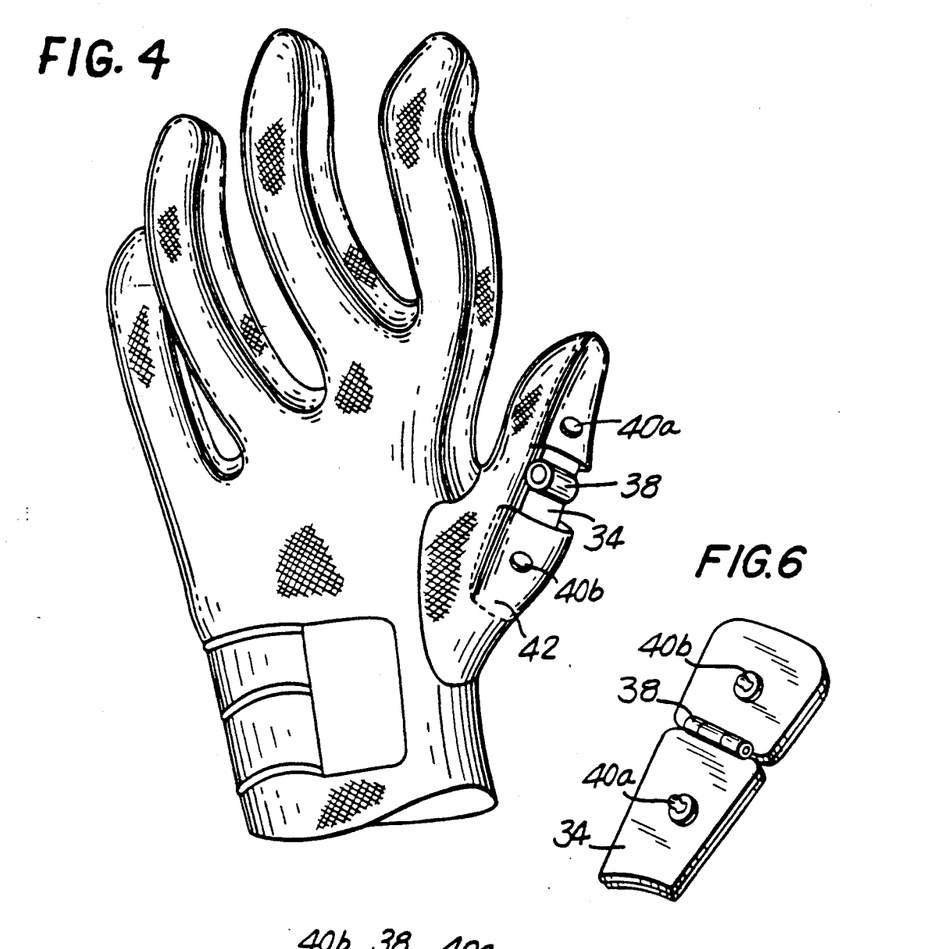
FIG. 4 is a side view of a hand guard according to the present invention.
FIG. 6 is a front view of protective material for the thumb according to the present invention.
Figure 5:
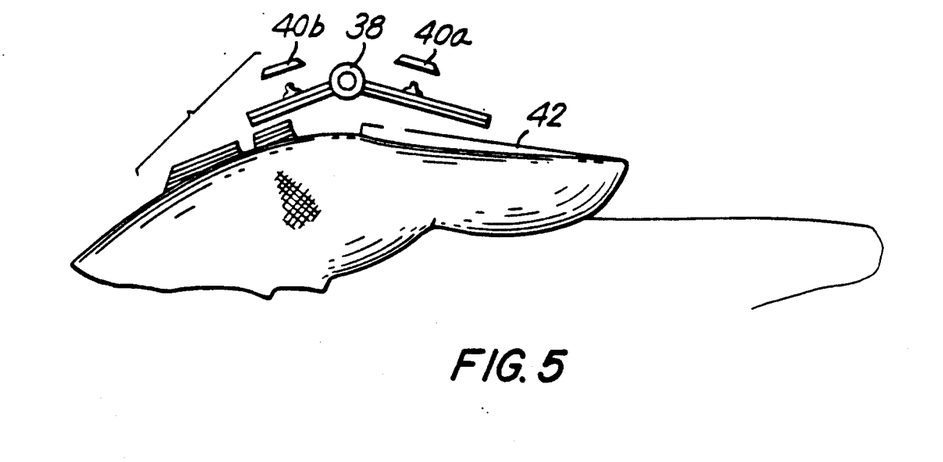
FIG. 5 is an exploded partial front view of a hand guard according to the present invention.
Figures 7, 8, 9, 9A:
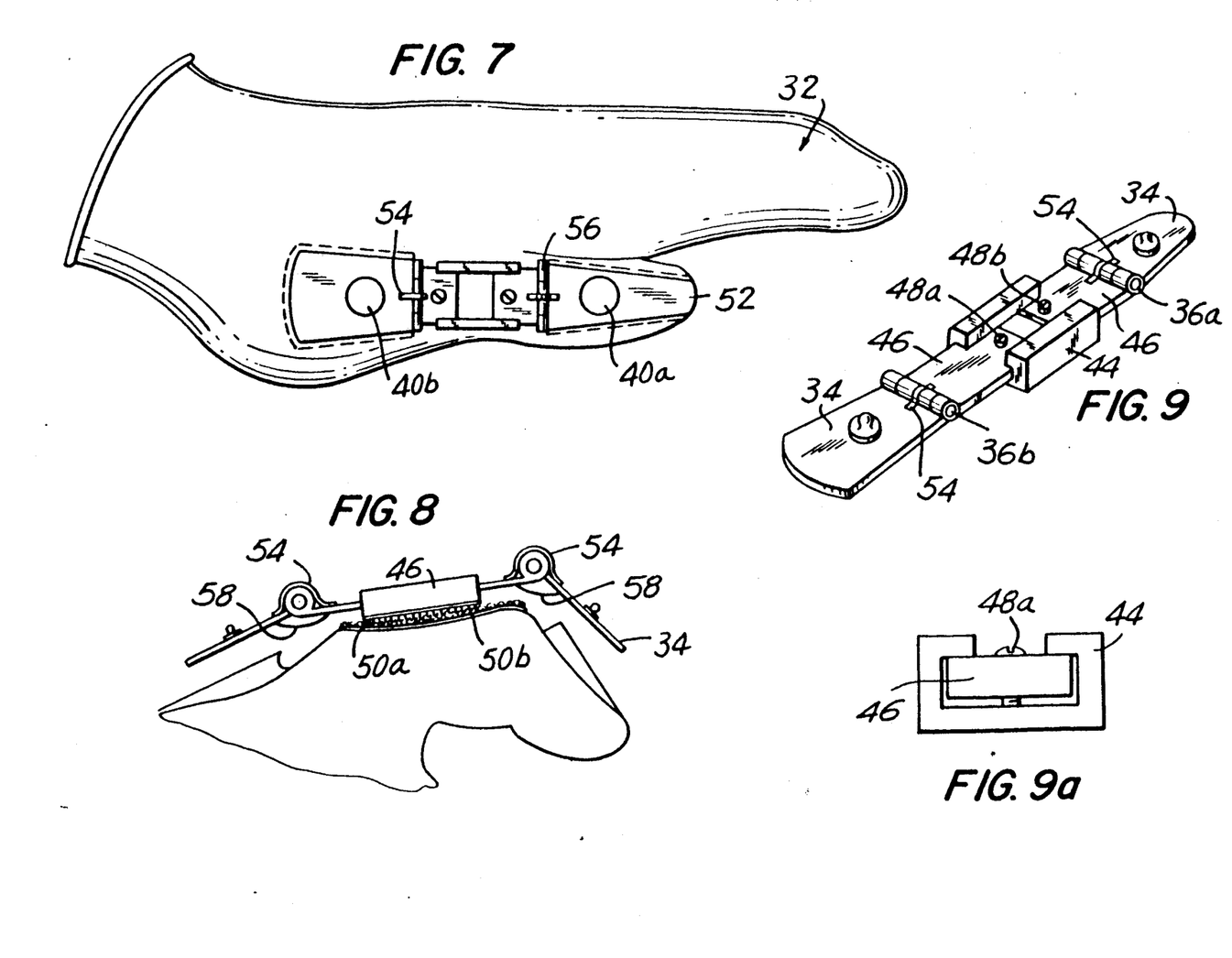
FIG. 7 is a side view of a hand guard according to the present invention.
FIG. 8 is an exploded partial front view of a hand guard according to the present invention.
FIG. 9 is a front view of protective material for the thumb according to the present invention.
FIG. 9a is a cross-sectional taken along line B—B of FIG. 9.

FIG. 4 and 5 illustrate another embodiment of the thumb guard according to the present invention. The rigid material 34 is snapped to leather material 42 by first snap 40a and second snap 40b.

FIG. 6 illustrates rigid material 34 with first and second snaps 40a, 40b and hinge 38.

FIG. 7, 8, 9 and 9a illustrate rigid material 34 provided with length adjustment means including adjustable slide mechanism 44, slot 46 and locking screws 48. First hinge 36a is adjacent the lower thumb joint and second hinge 36b is adjacent the upper thumb joint. As shown, rigid material 34 is uncovered between first hinge 36a and second hinge 36b, and velcro material 50a, 50b is provided on opposing adjacent surfaces of the under side of rigid material 34 between first hinge 36a and second hinge 36b and the back portion of the thumb of glove 32. The tip 52 of rigid material 34 extends as least to the tip of the thumb. First hinge 36a and second hinge 36b are each constructed so as not to bend past 180 degrees in a direction opposite the natural bending direction of the thumb. This feature gives the thumb support against hyperextension injuries.

Figure 10:
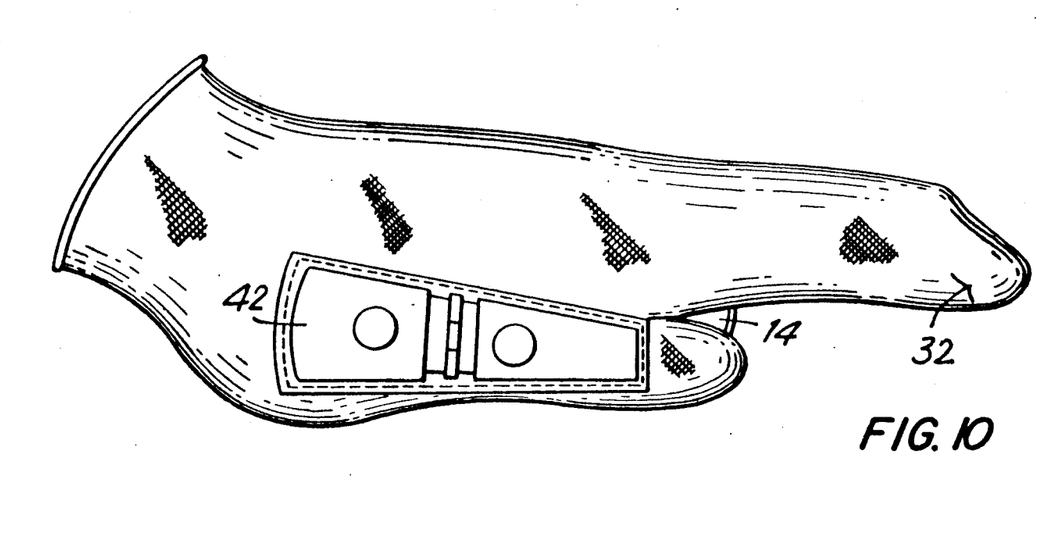
FIG. 10 is a side view of a hand guard according to the present invention.
Figure 11:
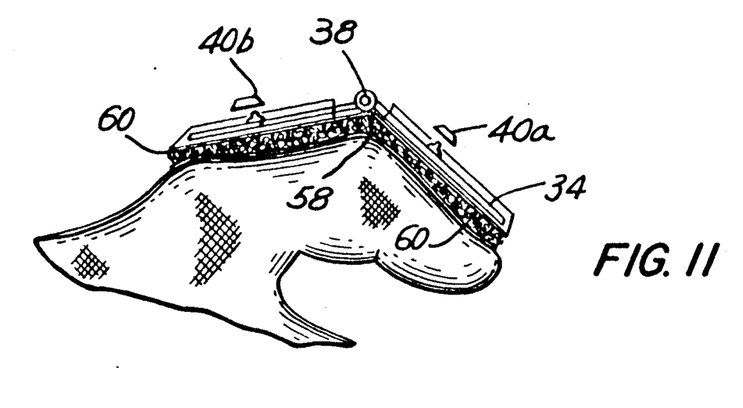
FIG. 11 is an exploded partial front view of a hand guard according to the present invention.

First hinge 36a and second hinge 36b are each configured and dimensioned so as not to bend towards the palm of the hand to an extend which would be an unnatural bending for the respective lower and upper thumb joints, so as to prevent sprains. As illustrated, first hinge 36a and second hinge 36b can be provided with belts 54 on the side facing away from the thumb and which can be firmly attached to rigid material 34 at points on opposite sides of each hinge and of such length so as to prevent excessive bending. The belts 54 can be either flexible or rigid with a bent portion to allow flexing, and can be attached to the respective hinge or be separate therefrom. Alternatively, rigid material 34 can be provided with a rigid stop protrusion 58 on the side facing towards the thumb at joints on opposite sides of the respective hinges so as to prevent bending, as illustrated in FIG. 11. FIG. 10 and 11 illustrate a thumb guard embodiment according to the present invention wherein a shock absorbing pad 60 is disposed between rigid material 34 and the thumb. Rigid material 34 is attached to shock absorbing pad 60 by adhesive, and the adjacent opposing faces of shock absorbing pad 60 and the thumb of glove 32 are provided with velcro material so as to be releasably attachable.

FIG. 10 also illustrates that glove 32 can be provided with both a finger guard according to the present invention comprising shock absorbing material 14 disposed adjacent the front of the forefinger joints and a thumb guard according to the present invention comprising a portion of rigid material 34 disposed adjacent the back side of the lower thumb joint.

Figure 13:
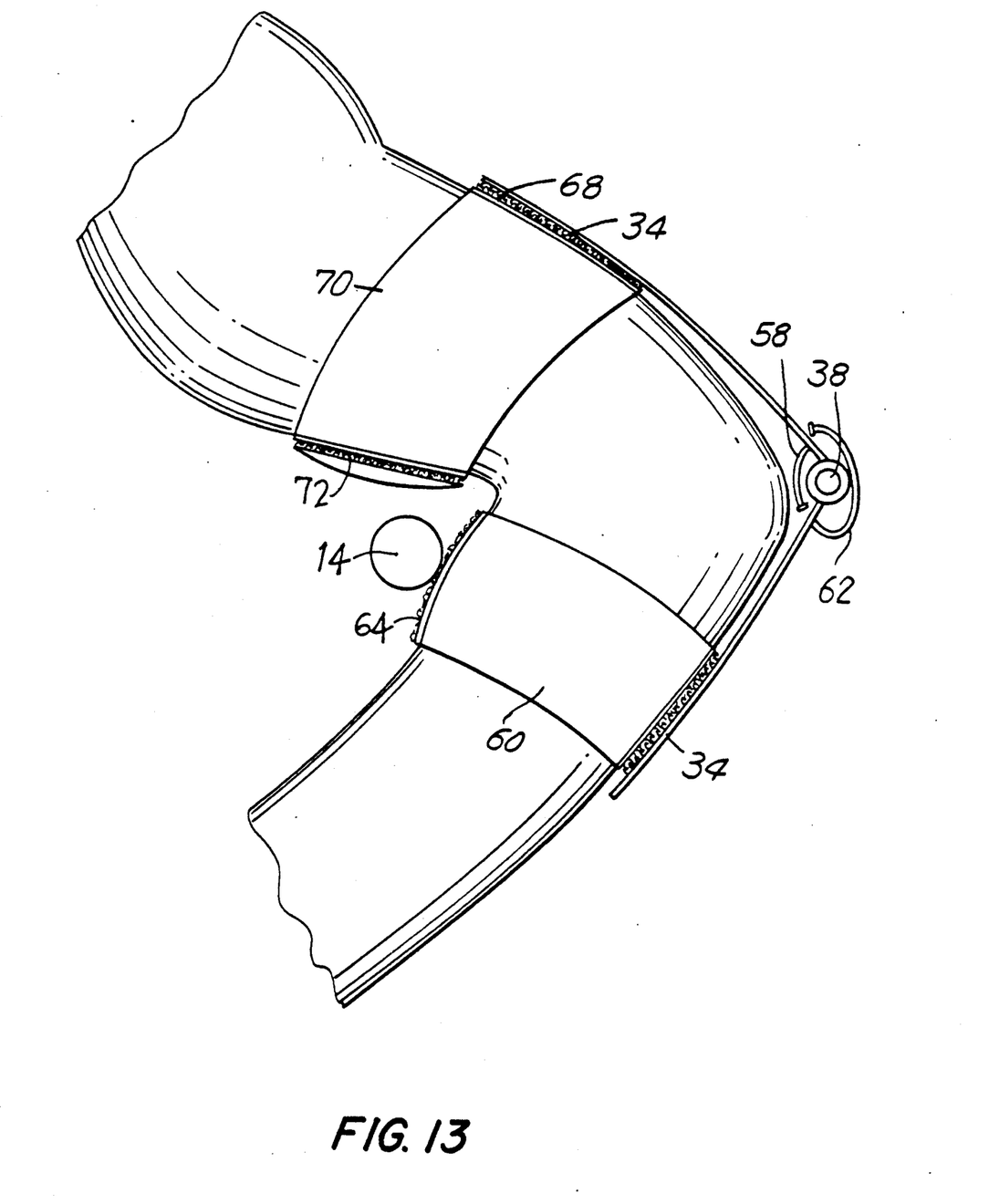
FIG. 13 is an exploded partial side view of a joint-/ligament guard according to present invention.
Figures 14, 15:
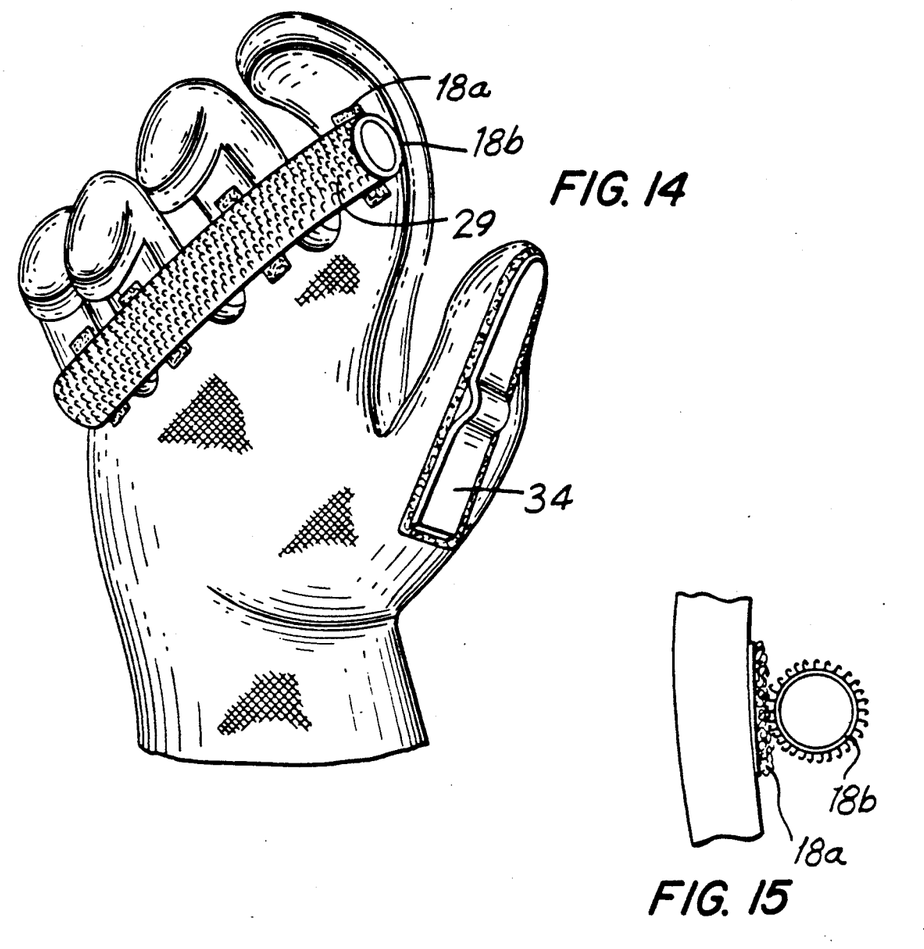
Figure 16:
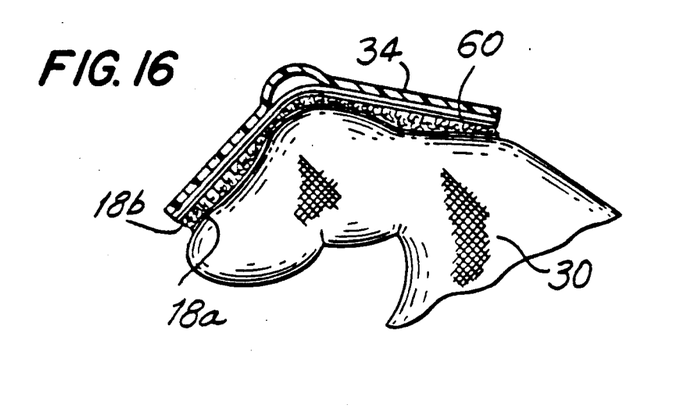

As illustrated in FIG. 13, devices according to the present invention can be used in relation with other joints, such as the elbow. Armband 60 is provided with a portion of velcro material 64 adjacent the front side of the elbow joint for releasable attachment to shock absorbing material 14, which is also provided with a portion of velcro material. Armband 60 is also provided with a portion of velcro material 66 adjacent the rear side of the elbow joint for releasable attachment to a portion of rigid material 34.

Armband 70, on the opposite side of the elbow, is provided with a portion of velcro material 68 adjacent the rear side of the elbow joint for releasable attachment to rigid material 34. Rigid material 34 is provided with hinge 38 which includes sprain stop 58 which includes a portion of rigid material on the front side of hinge 38 extending from a location adjacent rigid material 34 on the lower side of hinge 38 to a location adjacent rigid material 34 on the upper side of hinge 38 which is configured and dimensioned so as to prevent rigid material 34 from bending inward to a point which would be an unnatural, painful or injurious amount of bending for the elbow joint. Hinge 38 is also provided with hyperextension stop 62 which includes a portion of rigid material on the rear side of hinge 38 extending from a location adjacent rigid material 34 on the lower side of hinge 38 to a location adjacent rigid material 34 on the upper side of hinge 38 and which is configured and dimensioned so as to prevent rigid material 34 from bending outwards past 180 degrees so as to prevent any unnatural, painful or injurous hyperextension of the elbow joint. Sprain stop 58 and hyperextension stop 62 can be integral with or wholly apart from hinge 38. Armband 70 can also be provided with a portion of shock absorbing material 72 releasably attached thereto adjacent the front side of the elbow joint.

I claim:
1. A hand guard comprising:
 a glove having a front surface, back surface, finger portions, and a thumb portion;
 a segment of shock absorbing material having a cylindrical cross section and a length sufficient to span across all of said finger portions;

means for attaching said shock absorbing material to said front surface across said finger portions, such that when said glove is in use, said shock absorbing material covers the middle joint of each of the user's fingers.

2. The hand guard of claim 1 wherein the means for attaching comprises elastic strips attached with thread to each of said finger portions and extending over said shock absorbing material.

3. The hand guard of claim 1 wherein the means for attaching is releasable and comprises a patch of loop material secured to each of said finger portions, and an outer covering of hook material secured to said shock absorbing material.

4. The apparatus according to claim 1 wherein said shock absorbing material is releasably attached to said glove by said means for attachment having a tear-away threshold so as to allow said shock absorbing material to be removed from said clothing by a threshold force.

5. The hand guard of claim 1 further comprising a rigid protective material attached to said back surface on said thumb portion, said rigid protective material configured and dimensioned so as to prevent direct impact to the back side of the joint, said rigid protective material being provided with bending means, said bending means configured and dimensioned so as to allow said rigid protective material to bend in a manner approximating the natural bending of the joint and immediately connecting bones and so as to prevent bending of the rigid protective material to an extent which would be an unnatural and injurious amount of bending for the joint.

6. The hand guard of claim 5 wherein said bending means comprises a hinge.

7. The apparatus according to claim 5 wherein said rigid protective material and said bending means are configured and dimensioned so as to prevent said rigid protective material from bending in a direction opposite the natural bending direction of the joint so as to prevent the joint from bending in a direction opposite the natural bending direction of the joint.

8. The apparatus according to claim 7 wherein said rigid protective material is provided with more than one bending means at positions so as to allow positioning of said bending means adjacent each joint.

9. The apparatus according to claim 5 wherein said rigid protective material is provided with a length adjustment means.

10. The apparatus according to claim 9 wherein said rigid protective material is releasably attached to said glove by hook and loop fasteners.

* * * * *